(12) United States Patent
Peuscher (10) Patent No.: US 9,020,013 B2
(45) Date of Patent: Apr. 28, 2015

(54) APPARATUS AND METHOD FOR PROCESSING SIGNALS

(71) Applicant: Twente Medical Systems International B.V., Oldenzaal (NL)

(72) Inventor: Jan Hendrik Peuscher, Enschede (NL)

(73) Assignee: Twente Medical Systems International B.V., Oldenzaal (NL)

( * ) Notice: Subject to any disclaimer, the term of this patent is extended or adjusted under 35 U.S.C. 154(b) by 0 days.

(21) Appl. No.: 14/383,881

(22) PCT Filed: Mar. 1, 2013

(86) PCT No.: PCT/NL2013/050130
§ 371 (c)(1),
(2) Date: Sep. 8, 2014

(87) PCT Pub. No.: WO2013/133697
PCT Pub. Date: Sep. 12, 2013

(65) Prior Publication Data
US 2015/0036769 A1 Feb. 5, 2015

(30) Foreign Application Priority Data
Mar. 9, 2012 (NL) .................................... 2008441

(51) Int. Cl.
| | | |
|---|---|---|
| *H04B 1/38* | (2006.01) | |
| *H04L 5/16* | (2006.01) | |
| *H04L 25/06* | (2006.01) | |
| *H04B 1/16* | (2006.01) | |
| *A61B 5/04* | (2006.01) | |
| *A61N 1/365* | (2006.01) | |

(52) U.S. Cl.
CPC ................ *H04L 25/061* (2013.01); *H04B 1/16* (2013.01); *A61B 5/04004* (2013.01); *A61N 1/36521* (2013.01)

(58) Field of Classification Search
CPC ...................... A61B 5/04004; H03F 2200/153; A61N 1/36521; A61N 1/3702; H03M 1/12; H03M 1/66
USPC .................................. 375/219, 349; 600/547
See application file for complete search history.

(56) References Cited

U.S. PATENT DOCUMENTS

| | | | |
|---|---|---|---|
| 5,205,294 A | 4/1993 | Flach et al. | |
| 2006/0122529 A1* | 6/2006 | Tsau | 600/544 |

FOREIGN PATENT DOCUMENTS

| | | |
|---|---|---|
| WO | 2008/080008 A2 | 7/2008 |
| WO | 2009/017413 A1 | 2/2009 |

OTHER PUBLICATIONS

Rieger et al., "A Bio-Signal Amplifier system with Very-Large Dynamic-Range", Tencon 2007, 2007 IEEE Region 10 Conference, IEE, PI, Oct. 30, 2007, pp. 1-4, XP013226196.
Galjan, et al., "Highly Sensitive Biomedical Amplifier With CMRR Calibration and DC-OPffset Compensation", Eurocon 2009, IEEE, May 18, 2009, pp. 152-155, XP 031491839.
International Search Report dated Jun. 7, 2013 for PCT/NL2013/050130.

* cited by examiner

*Primary Examiner* — Curtis Odom
(74) *Attorney, Agent, or Firm* — Knobbe, Martens, Olson & Bear, LLP (57) ABSTRACT

An apparatus for processing signals, in particular physiological measuring signals, is provided with a number of channels with main signal inputs for receiving input signals. Each of the input signals has a specific signal component and a signal component common to all input signals. Each channel is provided with an impedance transforming input amplifier. The apparatus supplies a respective input signal to the first input of each input amplifier and an analog reference signal, which is equal for all channels, to the second input. The apparatus includes a digital signal processor and one or more analog-digital converters for supplying the signals provided by the input amplifiers to the digital signal processor. The signal processor converts signals received from the one or more analog-digital converters at least into one or more output signals.

22 Claims, 3 Drawing Sheets

APPARATUS AND METHOD FOR PROCESSING SIGNALS

RELATED APPLICATIONS

This application is the U.S. National Phase of International Application No. PCT/NL2013/050130, filed Mar. 1, 2013, designating the U.S. and published in English as WO 2013/133697 on Sep. 12, 2013 which claims the benefit of Dutch Patent Application No. 2008441 filed Mar. 9, 2012.

BACKGROUND OF THE INVENTION

1. Field of the Invention

The invention relates to an apparatus for processing signals, in particular physiological measuring signals, for instance EEG-signals (electroencephalogram signals), wherein the apparatus is provided with a plurality of channels with signal inputs for receiving input signals, which input signals each comprise a specific signal component and a signal component common to all input signals (also called a "common mode" signal), wherein each channel is provided with an impedance transforming input amplifier, wherein the apparatus is configured for supplying to a first input of each input amplifier a respective signal and to a second input an analogue reference signal which is equal for all channels.

2. Description of the Related Art

Such an apparatus is known from international application WO2009/017413, the content of which is incorporated by reference in its entirety. As follows from this publication, it has appeared that with particular measurements, for instance electrophysiological measurements, the input signals (E1, E2, E3, . . . , En,) can each contain various components.

A first component in each signal comprises, in particular, the electrophysiological information. A second component comprises, in particular, a mains interference signal. A third component comprises a sensor offset signal (in particular an electrode offset signal).

The electrophysiological information mentioned is in particular the important measurement part of the input signal and can have an amplitude in the range of, for instance, some microvolts to some millivolts.

Mains interference, in particular resulting from 50 Hz or 60 HZ mains AC voltage, is also called a "common mode disturbance". The amplitude of this interference can vary strongly, between, for instance, 1 and 100 mV.

A sensor-offset signal, in particular an electrode offset (the third component in an input signal) can have varying amplitudes, and is generally not stable. It can comprise a DC signal with an amplitude between 0 V and some hundreds of mVs, and can vary with a very low frequency.

Figure 1:
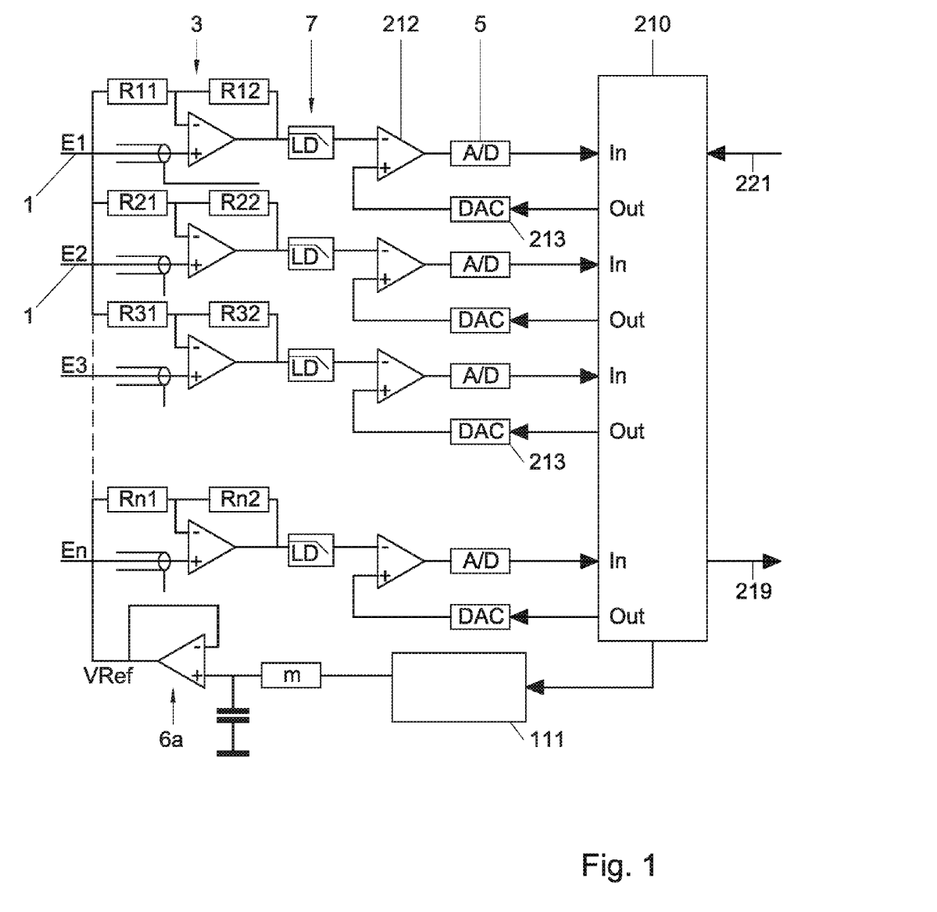
FIG. 1 shows an apparatus known from the state of the art.

An example of the know reference amplifier is depicted in FIG. 1. As follows from FIG. 1, a known compensated digital DC reference amplifier serves for processing signals, in particular physiological measuring signals supplied through sensors (not represented), and is provided with several (N) channels with N signal inputs 1 for receiving input signals. The input signals E1, E2, E3, . . . , En (with n being 1, 2, 3, . . . , N) each comprise a specific signal component and a signal component common to all input signals (the "common mode signal"). As follows from the above, the specific signal component may include an electrode signal as such, the electrode signal particularly including the afore-mentioned electrophysiological information and electrode offset signal.

Thus, for a particular period of time, one or more input signals E1, E2, E3, . . . , En can contain sensor related offset signal parts. Each channel is provided with an impedance transforming input amplifier 3. These amplifiers 3 are preferably operational amplifiers (Opamps). The apparatus is also provided with a digital signal processor 210, and several analogue-digital converters (A/D converters) 5, i.e. one per channel, for supplying the amplified signals provided by the input amplifiers 3, to the digital signal processor 210. The signal processor 210 is designed for converting signals received from the one or more analogue-digital converters 5 into at least one or more output signals, and outputting this/these, for instance, via a signal output 219. The signal processor 210 may be provided with, for instance, one or more other inputs, for instance a serial input 221 for communication with other modules or components.

The known apparatus is provided with low pass filters 7. An input of each filter 7 may be directly or indirectly coupled to the output of a respective input amplifier 3, of the same channel, for receiving the signal coming from this amplifier.

Following from WO2009/017413, the signal processor 210 may be designed for supplying a digital reference signal, which digital reference signal is converted into said analogue reference signal Vref by suitable converter means 111, 6a. In particular, the digital signal processor 210 may be designed to process, in particular digitally average, the digital signals received from the A/D converters 5, for providing the digital reference signal. Said averaging comprises, for instance, a summation step $\Sigma$ wherein the digital signals, coming from the N different channels, are added up, and a division step 1/N wherein the sum of the digital signals (i.e. the result of said summation step) is divided by the number N of those signals (i.e. the number of channels). The digital result of this operation comprises a digital reference signal, which is supplied via a signal output to a digital-analogue (D/A) converter (DAC) 111 (for instance a 20 bit D/A converter 111). This D/A converter 111 converts the digital reference signal into an analogue signal, which analogue signal is processed via an impedance transforming amplifier 6a for providing the analogue reference signal Vref. To this end, the output of the D/A converter 111 is coupled via a suitable impedance (in particular comprising a resistance m) to the first input (e.g. the non-inverting input) of this amplifier 6a, while the other (e.g. the inverting) amplifier input is electrically short-circuited to the amplifier output. As follows from the drawing, the analogue reference signal Vref is fed to only one of the inputs if each input amplifier 3 (i.e. only to the first input, and not to the second input).

In addition, the apparatus includes a second amplifier stage, comprising compensation amplifiers (in particular Op amps) 212 which are each arranged in a respective channel between a low pass filter 7 and A/D converter 5. In particular, a first input of each compensation amplifier 212 is arranged for receiving the low pass filtered amplified signal from a respective input amplifier 3, via a filter 7. An output of each compensation amplifier is directly coupled to an A/D converter 5 for providing a signal compensated by the amplifier 212 to the A/D converter 5, wherein the A/D converter supplies the digitized signal to a respective input (In) of the signal processor 210.

In the know apparatus, the second input of each compensation amplifier 212 is coupled via a suitable digital-analogue converter 213 to a respective output (Out) of the signal processor 210 for receiving a control signal therefrom. In this case, the signal processor 210 comprises, for instance, a microcontroller, with suitable software for carrying out various signal processing functions of the signal processor 210. These signal processing functions comprise, in particular: calculating a digital reference signal, producing suitable control signals to be supplied to the D/A converters 213 and providing output signals, via the (preferably serial) output 219. The signal processor 210 is designed for providing each control signal under the influence of and/or while utilizing one or more digital signals obtained from the analogue digital converters 5.

Following from WO2009/017413, the elaboration according to FIG. 1 has several advantages. For instance, a relatively high gain may be used, for instance 500× (for instance 10× in the input stage 3 and 50× in the compensation stage 212, or a different, suitable proportion), so that A/D converters 5 with a relatively low resolution, low disturbance, high sample frequency and virtually no delay may be used.

The publication "A Bio-Signal Amplifier System with Very-Large Dynamic-Range", Robert Rieger et al., Tencon 2007 IEEE region 10 conference, IEEE, 30 Oct. 2007 pages 1-4, describes the recording of very small signals such as body potentials, wherein a single amplifier is reset before it can leave its dynamic range. The feedback provided is not continuous. In FIG. 4 of the document, a discrete level offset is fed to both inputs of an OPAMP. Besides, the electrode signal is fed to both inputs of the OPAMP. According to the document, the sole purpose of the compensation voltage is to ensure that the amplifier always works within its intended operating region; removal of any residual offset is not required. A similar system and method is disclosed in U.S. Pat. No. 5,205,294.

WO2008/080008 discloses an operational amplifier circuit for conditioning analogue bioelectric signals, wherein both the inverting and non-inverting terminal are coupled to a common reference potential. A common reference potential can be generated inside an acquisition system, wherein a subject can be biased to the same potential.

The publication "Highly sensitive biomedical amplifier with CMRR calibration and DC-offset compensation", Eurocon 2009, IEEE, Piscataway N.J. USA, May 18, 2009 pages 152-155 discloses application of a switchable resistor array of a digitally controlled calibration circuit, for increasing a common mode rejection ratio. Electrode signals are fed to the non-inverting input of a amplifier, whereas both a common reference voltage and a dc-offset compensation voltage (Vdac) are fed to the inverting input. Due to the fact that mutually different Vdacs will be present in the different channels, so that amplification for each channel regarding the common mode signal will be different. It is required that a number of resistors are calibrated for each channel, to obtain a desired common mode rejection.

SUMMARY OF THE INVENTION

The present invention aims to provide an improved reference amplifier. Particularly, the invention aims to provide a reference amplifier that can achieve gains of over 500×, and providing improved signal quality.

To this end, the apparatus according to the invention is characterized by the features according to claim 1.

According to the invention, there is provided an apparatus for processing signals, in particular physiological measuring signals, wherein the apparatus is provided with a plurality of channels with main signal inputs for receiving input signals, which input signals each comprise a specific signal component and a signal component common to all input signals, wherein each channel is provided with an impedance transforming input amplifier, wherein the apparatus is configured for supplying to the first input of each input amplifier a respective input signal and, to the second input, an analogue reference signal which is equal for all channels, wherein the apparatus is provided with a digital signal processor and one or more analogue digital converters for supplying the signals provided by the input amplifiers to the digital signal processor, wherein the signal processor is designed for converting signals received from the one or more analogue digital converters at least into one or more output signals, wherein the signal processor is designed for processing, in particular digitally averaging, the signals received from the one or more analogue-digital converters, for providing a digital reference signal, wherein the apparatus is provided with a digital-analogue converter for converting the digital reference signal into said analogue reference signal, wherein each channel is provided with a dc-compensation means (i.e. direct-current compensation means), e.g. a compensation amplifier, wherein an input of the dc-compensation means is coupled via a digital-analogue converter to said signal processor for receiving a control signal therefrom, wherein the dc-compensation means are configured to compensate the input signals, received via main inputs, and arranged for providing the compensated input signals to the first inputs of the input amplifiers.

In this way, relatively high gains can be obtained as well as improved signal quality, and for example still using relatively low resolution A/D converters. For example, gains between 500 to 1000 times may be achieved. Also, the apparatus according to the invention is relatively energy-efficient, requiring relatively little operating power. Further, the apparatus may be manufactured in a relatively economical manner, using relatively inexpensive components, and can be made relatively compact. For example, a highly sensitive apparatus providing a relatively high resolution (e.g. 24 bits resolution or even higher) may be provided utilizing relatively low resolution analogue digital converters (e.g. A/D converters with a resolution lower than 20 bits, for example 12 bits A/D converters).

Moreover, the apparatus can achieve an amplification of a common mode signal of 1×. Thus, particularly, the configuration is such that signal processor actually "knows" the common mode signal.

In fact, the configuration can be such the signal processor can reconstruct the total input signal for each of the channels, the total signal particularly including the three components: 1) the specific electrophysiological information, 2) the common mode disturbance and 3) the specific electrode offset signal.

Therefore, contrary to any of the prior art systems, in the present reference amplifier, the common mode signal may generally have an amplification of 1×, whereas the electrode signals may be amplified by at least 500×. It follows that a common mode rejection ration can be increased by a factor of e.g. 500 times.

It follows that offset per channel may be compensated well, in a relatively simple manner, so that the amplification per channel no longer depends on the offset variances, but only on the electrophysiological signal characteristics (i.e. the specific signal components mentioned). Furthermore, the capacity to remove common signal components from the signals can thus be improved considerably, while power consumption can decrease.

In a further embodiment, the at least one A/D convertor is operated at a sample frequency of at least 30 kHz.

Particularly, the apparatus is configured to prevent dc-signal offsets in the primary references amplifier stage, so that a common mode rejection ratio in that stage may be increased (e.g. by 500 times), so that the range of the amplifier may be extended and the amplifier signal output power can be optimised.

Furthermore, application of high-pass filters in the reference amplifier stage may be avoided, so that low frequency input signals (e.g. having a frequency in the milli-Hertz range) may be processed by the apparatus.

For example, according to an embodiment, an output of each input amplifier may be operatively connected to an input of the at least one analogue-digital converter, directly or indirectly, without presence of a high-pass filter there-between.

According to an embodiment, the signal processor is designed for supplying each said control signal under the influence of and/or while utilizing one or more signals obtained from the, or one or more analogue-digital converters, respectively.

According to an embodiment, the signal processor is designed for detecting a signal offset voltage (i.e. a dc-offset) for each channel, and for adapting said control signal for removing at least a part of a detected signal offset voltage from an input signal to provide a compensated input signal.

According to an embodiment, the apparatus is provided with a multiplexer and one analogue-digital converter. The arrangement may for example be configured such that the multiplexer supplies the signals coming from said channels in a predetermined order to the analogue-digital converter. Alternatively, the arrangement may be configured such that the multiplexer supplies the signals coming from said channels in a random order to the analogue-digital converter.

According to a further embodiment, the signal processor may be configured to provide a first operational state including a full or substantially full dc-compensation for each channel by the dc-compensation means. Also, according to a further elaboration, the signal processor may be configured to provides a second operational state wherein no or only a partial dc-compensation is carried out by the dc-compensation means. Particularly, in the latter state, dc-compensation means control signals may be set by the signal processor to reduce dc-compensation or to refrain from any dc-compensation of the input signals.

The invention further provides a corresponding method according to the features of claim 13, providing the above-mentioned advantages.

The invention further provides software which is provided with a program code executable by a computer or processor, which program code is designed for having a computer or compressor function as a signal processor of an apparatus according to the invention when the code executed by the compressor or processor, respectively.

BRIEF DESCRIPTION OF THE DRAWINGS

The invention will presently be elucidated in further detail on the basis of the Figures, in which.

DETAILED DESCRIPTION OF THE PREFERRED EMBODIMENT

In this application, identical or corresponding features are indicated with identical or corresponding reference numerals.

Figure 2:
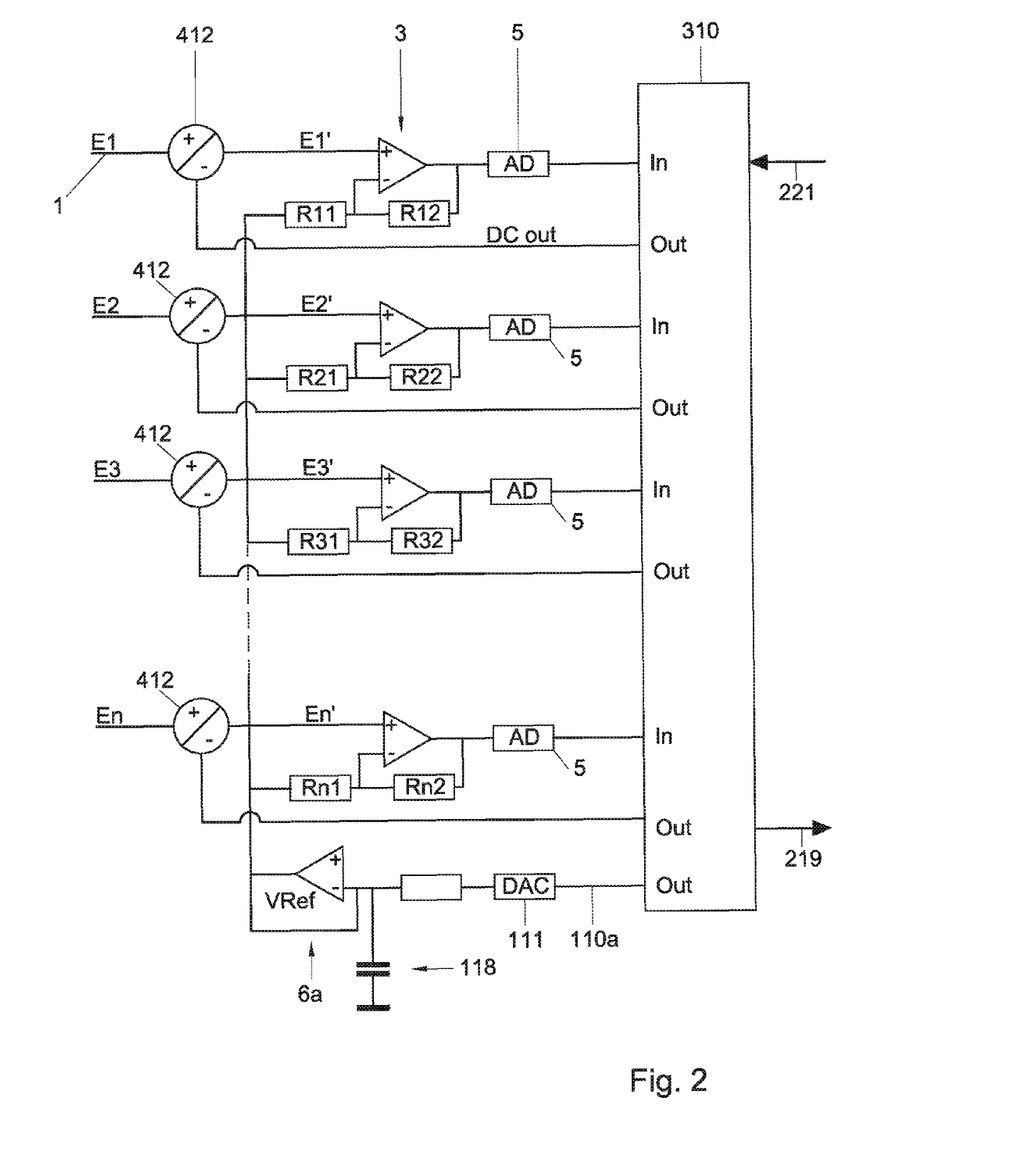
FIG. 2 shows a first exemplary embodiment of the present invention.

FIG. 2 shows a first non-limiting embodiment of an apparatus according to the invention.

The apparatus, in particular, is a DC reference amplifier. The apparatus represented in FIG. 2, which serves for processing signals, in particular physiological measuring signals supplied through sensors (not represented), is provided with several (N) channels with N signal inputs 1 for receiving input signals, which input signals E1, E2, E3, . . . , En (with n being 1, 2, 3, . . . , N) each comprise a specific signal component and a signal component common to all input signals. Furthermore, for a particular period of time, one or more input signals E1, E2, E3, . . . , En may contain sensor related offset signal parts, as is described hereinabove.

Preferably, the different channels (also called signal paths) may be designed in the same manner. Each channel is preferably provided with an impedance transforming input amplifier 3. These amplifiers 3 are preferably operational amplifiers (Opamps).

The present apparatus differs from the apparatus shown in FIG. 1 in that the is configured for supplying to the first input of each input amplifier 3 a respective compensated input signal E1', E2', E3', . . . , En' and, to the second input, an analogue reference signal Vref common to all channels, for providing an associated amplifier output signal via an output of the input amplifier 3. In the present embodiment, said first inputs of the input amplifiers 3 may be non-inverting inputs of these amplifiers 3, and said second inputs of the input amplifiers 3 may be inverting inputs of these amplifiers 3. The compensated input signal E1', E2', E3', . . . , En' of the embodiment of FIG. 2 are provided by dc-compensation means 412 as will be described below.

In FIG. 2, the apparatus is provided with an averager which is designed for forming the reference signal. In particular, the second input of each input amplifier is communicatively coupled, by means of a first respective impedance R11, R21, R31, . . . , Rn1 to an output of the averager, for receiving the reference signal Vref. Furthermore, by means of a second respective impedance R12, R22, R32, . . . , Rn2, the second input of each input amplifier 3 is brought into signal connection with the output of this amplifier.

The first impedances R11, R21, R31, . . . , Rn1, may be resistances wherein, according to a relatively simple design, all resistances R11, R21, R31, . . . , Rn are preferably identical. The same holds for the second impedances R12, R22, R32, . . . , Rn2. As will be clear to the skilled person, the gain supplied by each input amplifier 3 is set by the ratio between the respective first and second resistance.

In the present embodiment, the apparatus is provided with a digital signal processor 310, and several analogue-digital converters (A/D converters) 5, i.e. one per channel, for supplying the amplified signals provided by the input amplifiers 3, to the digital signal processor 10.

The signal processor 310 is designed for converting signals received from the one or more analogue-digital converters 5 into at least one or more output signals, and outputting this/these, for instance, via a signal output 219. The signal output 219 may be designed in different manners, and for instance comprise a digital output, in particular a serial output, and can for instance be suitable for supplying output signals relating to a large number of channels (for instance 128 channels, or another number). An output signal supplied by signal processor 310 may for instance comprise a digital signal stream, which is provided with the digital signals coming from the different channels, for instance in a predetermined order. Alternatively, the signal processor 310 may be designed for parallel outputting of the digital signals coming from the different channels via a parallel signal output (not represented).

Contrary to the apparatus shown in FIG. 1, the exemplary embodiment according to FIG. 2 is not provided with low pass filters 7 in the signal paths/channels between the outputs of the input amplifiers and the respective analogue-digital converters 5. Particularly, outputs of the input amplifier 3 are operatively connected to the input of the at least one analogue-digital converter 5, directly or indirectly (e.g. via a multiplexer, as in FIG. 3), without presence of a high-pass filter there-between. Thus, the apparatus may detect low frequency signals during operation. Besides, preferably, as follows from the drawings, the different channels of the apparatus themselves are not provided with high pass filters, so that the adverse effects of a sustained saturation resulting from the time constant of such a high pass filter may be avoided. It should be noted that in the apparatus shown in FIG. 1, no high pass filters are present in the signal paths/channels between the outputs of the input amplifiers and the respective analogue-digital converters 5.

The analogue reference signal Vref may be provided in several ways. For example, the apparatus may be provided with an analogue averager (not depicted) which is designed for forming the reference signal. For example (as has been described in WO2009/017413), an analogue averager may be communicatively connected to outputs of the input amplifiers 3, via signal connections which are located signal-upstream with respect to the low pass filters 7. The analogue averager may be provided with an impedance transforming amplifier (preferably an Op amp), of which an output is coupled in particular to the second inputs of the input amplifiers 3, via said first impedances R11, . . . , Rn1 for supplying said reference signal Vref to the input amplifiers 3. The analogue averager may be provided in a simple manner with a series of parallel arranged third impedances, in particular third resistances r1, r2, r3, . . . , rn which are preferably identical to each other, and which couple the outputs of the input amplifiers 3 to a first input of the averaging amplifier. The second input and output of the amplifier of the averager may then be directly coupled, via a signal connection. In other words: the amplifier of the averager is provided in an input-follower configuration, and thus provides for a gain 1× with a high input impedance and low output impedance, which configuration is generally known per se.

The A/D converters can be configured in various ways. In one embodiment, each of the A/D converters 5 may have a high dynamic range. To this end, use can for instance be made of A/D converters of a resolution of 20 bits or higher, for instance a resolution of 21 or 22 bits, or a different resolution. Example: suppose that an analogue-digital range is approximately ±3 Volts and the LSB (least significant bit) resolution is 1 microvolt, the number of bits of the A/D converter 5 should then be at least 22 bits (21 bits is sufficient for 3 Volt; therefore, for +3 and −3 Volt, the resolution should be 22 bits, the 'sign bit' included), which will be clear to the skilled person. If the input stage of the apparatus (comprising the input amplifiers 3) is for instance configured for supplying a gain of 20×, an A/D converter resolution of 0.07 microvolts LSB follows.

Advantageously, low resolution A/D converters 5 are applied. For example, according to a further embodiment, a maximum resolution of each of the A/D converters 5 may be 19 bits, particularly 18 bits, 17 bits, 15 bits, 14 bits, 13 bits or 12 bits. The apparatus may be configured to provide a signal output having a resolution that is at least twice the resolution of a said A/D convertor 5. For example, the apparatus may be configured to provide a signal output at a resolution of 24 bits utilizing 12 bits A/D converters 5. To this aim, particularly, the A/D converters 5 can be operated at a sample frequency of at least 30 kHz, allowing digital oversampling for increasing the resolution of the output signal.

The signal processor 310 may comprise, for instance, a digital signal processor (DSP), and may be provided by hardware, software or a combination thereof. The signal processor 310 itself may be designed for processing digital signals received from the A/D converters 5 such that certain sensor related offsets in those signals are substantially removed from the signals. To this end, the signal processor 310 may for instance be designed for detecting such offsets. Here, processing of the data is preferably such that a detection and modification of a digital signal part coming from one of the channels mentioned has no influence on the digital signal parts coming from the other channels.

Optionally, the signal processor 310 may be designed for carrying out a high pass filtering of each of the digital signals received from the A/D converters while utilizing, for instance, one or more suitable high pass filters designed in software.

In an advantageous embodiment, the signal processor 310 is only designed to receive the digital data streams received from the A/D convertors 5 and convert these into one digital output signal stream, wherein the signal processor 310 utilizes no digital signal offset compensation and, for example does not carry out high pass filtering. The output signal stream can for instance be processed further by a data processor (for instance computer, not represented) and/or may be saved. Such a data processor can for instance comprise suitable hardware and/or software, which is designed for detecting signal offsets in the output signal steam, per channel, and for removing the detected offsets for each channel. The data processor (not represented) can for instance be designed for carrying out a high pass filtering of the digital channel parts received from the signal processor 310.

In the present exemplary embodiment, it is further advantageous when a data processor is designed for digitally detecting the signal component common to all input signals (the common mode signal). Then, the data processor can process the received signals for removing a detected common signal component from the signals (however, this is not a dc-compensation for each channel as such). Thus, with additional advantage, the data processor can take over the function of analogue signal compensation means, per channel.

In the example shown in FIG. 2, the signal processor 310 is designed for supplying a digital reference signal, which digital reference signal is converted into said analogue reference signal Vref by suitable converter means 111, 6a. The apparatus is in particular provided a digital signal averager 310.

The digital signal processor 310 is designed to process, in particular digitally average, the digital signals received from the A/D converters 5, for providing the digital reference signal. Said averaging comprises, for instance, a summation step Σ wherein the digital signals, coming from the N different channels, are added up, and a division step 1/N wherein the sum of the digital signals (i.e. the result of said summation step) is divided by the number N of those signals (i.e. the number of channels). The digital result of this operation comprises a digital reference signal, which is supplied via a signal output 110a to a digital-analogue (D/A) converter (DAC) 111 (for instance a 20 bit D/A converter 111). This D/A converter 111 converts the digital reference signal into an analogue signal, which analogue signal is processed via an impedance transforming amplifier 6a for providing the analogue reference signal Vref. To this end, the output of the D/A converter 111 is coupled via a suitable impedance (in particular comprising a resistance m) to a first input of this amplifier 6a, while the second amplifier input is electrically short-circuited to the amplifier output. In this case, the first amplifier input is preferably earthed via a condenser 118.

The signal processor 310 is further provided with an output 219 for outputting output signals (see above). Optionally, the signal processing is integrally provided with digital high pass filters, for instance designed in software, for filtering signal components below a particular cut-off frequency from the signals. It will be clear to the skilled person how such a digital high pass filter, as such, may be designed. Preferably, the digital high pass filtering is not carried out before the summation step Σ is carried out, so that, also, an average offset signal becomes part of the reference signal, and the amplification of the input op amps 3 may be based on the variance of the offset signals. Here, a cut-off frequency of each digital high pass filter may for instance be 1 Hz or less, in particular 0.1 Hz or less, more particularly 0.01 Hz or less, in particular for substantially removing DC components from the digital signals.

In a preferred embodiment, the apparatus is configured for processing low frequency input signals, e.g. input signals having a frequency in the milli-Hertz range. In that case, for example the signal processor 310 does not provide an aforementioned digital high pass filtering, or a high-pass filtering having a cut-off frequency that is below the milli-Herz range.

The apparatus represented in FIG. 2 therefore comprises a digital DC reference amplifier, provided with digital components for calculating the reference signal. The calculation (comprising, for instance, the summation step Σ and division step 1/N) of the digital reference voltage may for instance be carried out by suitable software of the signal processor 310. In a further elaboration, the signal processor 310, such as in the exemplary embodiment represented in FIG. 2, may process the signals such that specific sensor related offsets are removed from the signals, per channel.

Besides, in the example of FIG. 2, a compensation stage is provided, comprising dc-compensation means 412 for each of the channels. The dc-compensation means may include for example compensation amplifiers 412, for example Opamps, or different types of dc-compensation means, for example digital or analogue voltage subtraction means, as will be appreciated by the skilled person.

An input of each of the dc-compensation means 412 is coupled directly or indirectly to a respective output ("Out") of the signal processor 310, for receiving a control signal ("DC OUT") there-from. The dc-compensation means 412 are configured to compensate the input signals E1, E2, E3, . . . , En, received via main inputs 1, and for providing the compensated input signals E1', E2', E3', . . . , En' to the first inputs of the input amplifiers 3. As follows from the drawings, particularly, the dc-compensation means 412 are arranged and controllable—by the signal processor 310 to compensate the input signals E1, E2, E3, . . . , En, received via main inputs 1, and for providing the compensated input signals E1', E2', E3', . . . , En' to the first inputs of the input amplifiers 3.

The dc-compensation means 412 may be provided with an analogue control signal input for receiving an analogue control signal, which input may be connected to the signal processor 310 via an intermediate digital-analogue converter. The latter digital-analogue converter may convert a digital control signal, provided by the signal processor 310, into the analogue control signal for controlling the dc-compensation means 412.

Alternatively, the signal processor 310 may itself include a digital-analogue convertor for outputting the analogue control signal, to be fed to the dc-compensation means 412.

Alternatively, the dc-compensation means 412 may be provided with a digital control signal input for receiving a digital control signal from the signal processor 310.

In a non-limiting embodiment, the dc-compensation means 412 include compensation amplifiers, e.g. Opamps which are each arranged in each respective channel, upstream with respect to the input amplifiers 3. In particular, a first (for example a non-inverting input) of each compensation means 412 may be arranged for receiving the input signal from a respective signal input 1, wherein a second (for example an inverting) input of each of the compensation means 412 may be coupled directly or indirectly to the signal processor 412 for receiving the control signal ("DC out").

In the present exemplary embodiment, an output of each compensation means 412 is directly coupled to an input of the input amplifier 3 of the same channel, for providing a signal E1', E2', E3', . . . , En' compensated by the compensation means 412 thereto.

In this case, the signal processor 310 may comprise, for instance, a microcontroller, with suitable software for carrying out various signal processing functions of the signal processor 310. These signal processing functions comprise, in particular: calculating a digital reference signal, producing suitable control signals to be supplied to the dc-compensation means 412 and providing output signals, via the (preferably serial) output 219.

The signal processor 310 may further be provided with, for instance, one or more other inputs, for instance a serial input 221 for communication with other modules or components. According to a further elaboration, the input 221 can communicate with, for instance, other modules, so that improved modularity and synchronisation with respect to other signal systems, and the flexibility with regard to extension of the number and types of channels may be obtained.

According to a further elaboration, the signal processor 310 is designed for providing each control signal ("DC out") under the influence of and/or while utilizing one or more digital signals obtained from the analogue digital converters 5.

Preferably, the signal processor 310 is designed for detecting a signal offset voltage for each channel (at least, a channel-specific offset, for instance a electrode offset mentioned) as such, and for adapting the control signal such that the respective dc-compensation means 412 can remove at least a part of the signal offset-voltage from the signal under the influence of this control signal—supplied thereto during operation.

In particular, from each channel an average offset potential and amplified offset variance is then compensated so that the respective compensation means 412 only passes the physiological component and a part of the common component (the common component, if any, being the common part not belonging to the low frequent offset). Even the use of different electrode materials is thus an option.

Preferably, the signal processor 310 is configured to detect, during a particular measuring period, a low frequent offset voltage variation for each channel (at least, a channel-specific offset).

If the signal processor 310 detects, for instance, that in the second channel (with respect to the second input signal E2), during a particular measuring period, a particular low frequent offset voltage variation is present, the signal processor 310 can control the respective compensation means 412 located in that channel, via the respective digital output ('out (2)'), to compensate the detected the offset variance. As an example, in case the compensation means 412 of a channel include an Opamp, a detected voltage variation may be supplied to one of the inputs of the Opamp whereas the other input receives the input signal from the respective channel input 1, so that the output of the Opamp provides the compensated input signal. During use, the average offset and the offset variance are preferably completely compensated. In this manner, the average of the offset still present can be 1× amplified in the signal, and the offset variance may be completely compensated.

The signal processor 310 needs not distinguish the offset variance. This very low frequent and fairly high amplitude of the offset signal is for instance digitally known, in processor 310, and may be removed from the signal by means of compensation means 412. As a result, a substantially physiological signal remains. This signal is additionally amplified and digitized. In the signal processor 310, the compensated offset and the digitized physiological component may be joined into one digital signal, if this is required. Owing to the additional amplification, for instance A/D converters 5 with relatively low resolutions may be used.

According to a further elaboration, the signal processor 310 may be arranged to take the specific design of the compensation stage (i.e. the configuration of all the compensation means 412) into account for producing an accurate signal offset compensation per channel. For example, in the case that the compensation means 412 include compensation amplifiers (e.g. Opamps), the signal processor 310 may be provided with calibration data with respect to linearity and gain of these compensation amplifiers, which calibration data are for instance used by the signal processor 310 when determining the control signals. Such calibration data can for instance be saved in a memory (not specifically represented) of the signal processor 310, and for instance be pre-entered or be determined by the signal processor 310 via a suitable calibration step. With such a calibration step, known input signals may be supplied to the inputs 1 of the apparatus. An optional compensation stage calibration can also comprise a different calibration method, which will be clear to the skilled person.

In the exemplary embodiment of FIG. 2 too, it is advantageous when the signal processor 210 is designed to carry out a high pass filtering of each of the digital signals received from the A/D converters 5.

The elaboration according to FIG. 2 has several advantages. For instance, a relatively high gain may be used, for instance higher than 500× (for instance more than 10× in the input stage 3 and 50× in the compensation stage 412, or a different, suitable proportion, so that A/D converters 5 with a relatively low resolution, low disturbance, high sample frequency and virtually no delay may be used. In this manner (for instance physiological) measuring signals may be distinguished from other signal parts particularly well and be detected. In particular, as is mentioned before, offset per channel may be compensated well, so that the amplification per channel no longer depends on the offset variances, but only on the electrophysiological signal characteristics (i.e. the specific signal components mentioned). Furthermore, the capacity to remove common signal components from the signals can thus be improved considerably, while power consumption can decrease.

The apparatus shown in FIG. 2 may obtain very high gains (e.g. up to 1000×). Due to the fact that in a channel any DC-offset may entirely be compensated before the signal is fed into the reference amplifier stage (provided by the input amplifiers 3), just a common mode signal and the electrode signals may be amplified. In the reference amplifier stage, the common mode signal generally has an amplification of 1×, whereas the electrode signals may be amplified by at least 500×. It follows that a common mode rejection ration can be increased by a factor of e.g. 500 times. Besides, the apparatus provides for processing of low frequency electrode signals.

Figure 3:
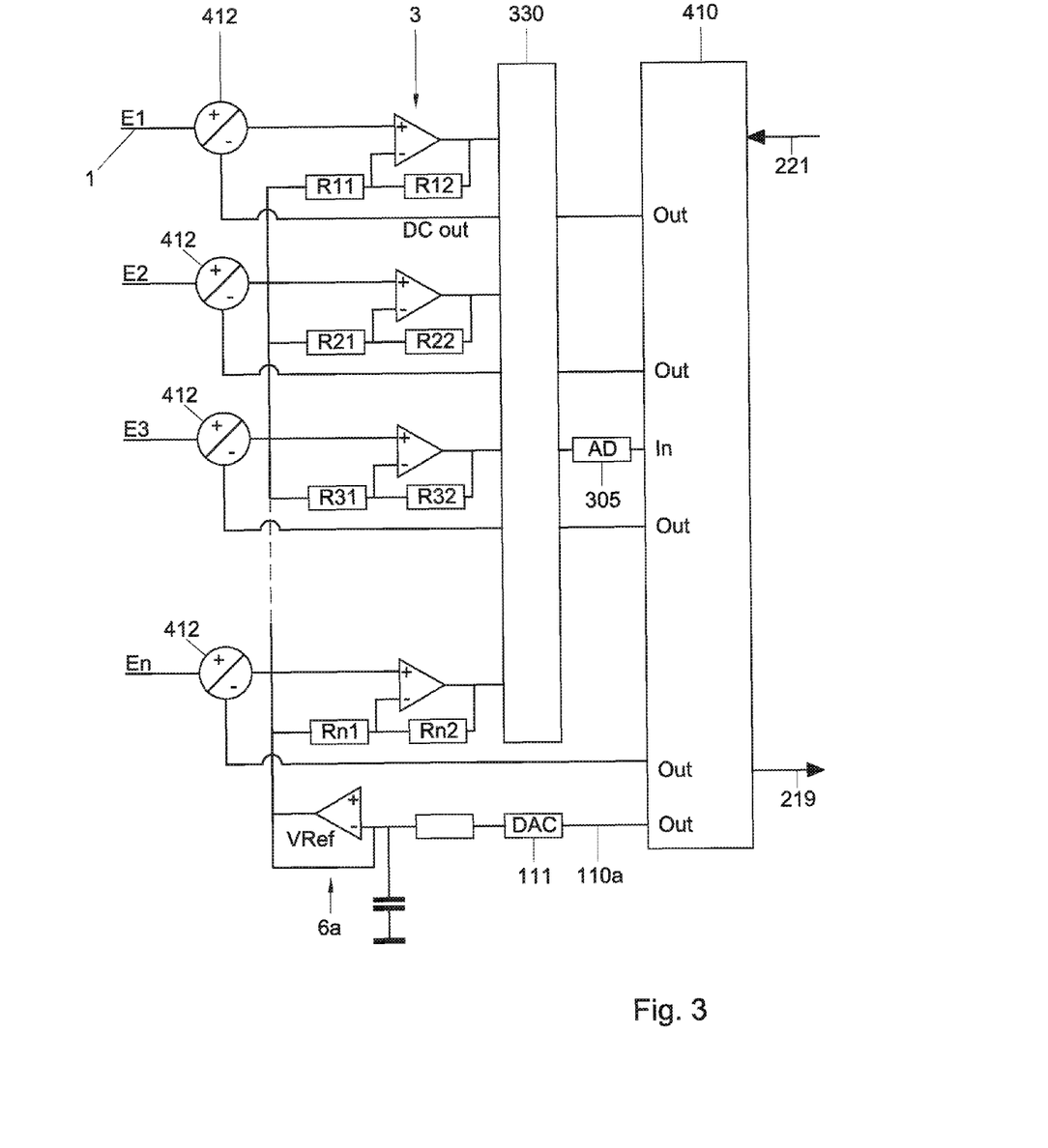
FIG. 3 shows a second exemplary embodiment of the present invention.

FIG. 3 shows a further advantageous elaboration of the invention, which is based in particular on the elaboration according to FIG. 2.

As shown in FIG. 3, it is advantageous when the apparatus is provided with a multiplexer 330 and only one analogue-digital converter 305, wherein the arrangement is set up such, at least coupled to each other such that the multiplexer 330 supplies the amplified signals coming from the various channels in a predetermined order to the analogue digital converter 305. The A/D converter supplies the successively digitized signals to the signal processor 410. In the present exemplary embodiment, the inputs of the multiplexer 330 are coupled to outputs of the input amplifiers 3.

The multiplexer 330 can operate in various ways. For example, the arrangement may be configured such that the multiplexer supplies the signals coming from said channels in a predetermined order to the analogue-digital converter. Alternatively, the arrangement may be configured such that the multiplexer 330 supplies the signals coming from said channels in a random order to the analogue-digital converter.

According to an elaboration, the multiplexer 330 may be designed to, during use, periodically alter the predetermined order for the N different channels. Preferably, the alteration takes place each time all N channels have been "addressed" once (at least, each time the signal of each of the N channels has been transmitted once by the multiplexer 330 to the A/D converter 305), while the order preferably comprises an alternately increasing and decreasing order, from a first channel (n=1) to last channel (n=N) and vice versa. In the latter case, the order of the channels of which the multiplexer 330 transmits the signal to the A/D converter 305 is, for instance, in the channel order (for channels 1, 2, ..., N): n=1, n=2, ..., n=N−1), n=N, n=N, n=(N−1), n=(N−2), ..., n=2, n=1, n=1, n=2, ..., n=(N−1), n+N, n=N, n=(N−1), n=(N−2), ..., n=1, etc. Another order, other than an each time the same order for a number of N channels, is possible too.

In this manner, a simpler and more compact system may be obtained, with fewer components, which furthermore consumes less power. Through the use of the repeatedly altering multiplexer signal transmission order, multiplexer related phase problems, which could in particular arise when using the optional compensation amplification stage if such an order is not utilized, may be avoided.

The present invention can offer various advantages, as has already been described hereinabove. The invention can in particular present an apparatus wherein different signals may be processed via different channels, for amplifying specific signal components, for the purpose of detection, and, in particular, for distinguishing the specific components of common signal components (separation of specific signal components and common components may be carried out by the apparatus itself, or, for instance, by digital signal processing means arranged downstream). Here, in particular, a relatively high gain may be utilized on the input signals by an amplifier stage 3 located signal-upstream, for instance a gain of 50× or more, in particular 100× or more, or another value.

Here, in particular a digital circuit, at least a digital signal processor 310, 410 is integrated into the apparatus. The apparatus is preferably designed such that DC components typically present in the input signals (for instance DC offset parts) can reach the digital signal processor via respective channels, wherein the channels are preferably not provided with DC filtering means.

A common signal component can for instance be digitally calculated from digital information. Preferably, a feedback loop 111, 6a is available for feeding a digitally calculated common signal component as reference signal back to the reference amplifier part 3 of the apparatus.

More preferably, furthermore, a specific offset per channel is calculated by the digital signal processor (for instance by suitable software of the digital signal processor) while utilizing the signals digitized by the A/D converter(s) 5, 305. The thus calculated specific offset can then simply be compensated, per channel, via said compensation stage.

In any case, removing a signal component (in particular a mains component, for instance a 50 Hz or 60 Hz AC component) common to all input signals from the analogue input signals is preferably completely controlled by/via the digital signal processor 310, 410 while utilizing the signals digitized by the A/D converter(s) 5, 305.

Besides, the apparatus may be operated in a mode of operation that provides no or only a partial dc-compensation by said dc-compensation means 412. For example, the signal processor 310, 410 may be configured to set the apparatus in various operational states, one state including a full or substantially full dc-compensation for each channel by the dc-compensation means, and a second state wherein no dc-compensation is carried out by the dc-compensation means. In the second operational state, e.g., the signal processor 310, 410 may provide a control signal "DC out" to the dc-compensation means 412 such that these dc-compensation means 412 pass the input signals E1, E2, E3, . . . , En without altering those signals, or without substantially altering those signals (i.e. E1'=E1 or E1'≈E1 . . . En'=En or En'≈En).

Also, for example, the first input of each said impedance transforming input amplifier can be an inverting or non-inverting input of that amplifier, wherein the respective second input of that amplifier can be a non-inverting input or inverting input, respectively, of that amplifier.

What is claimed is:

1. An apparatus for processing signals wherein the apparatus comprises:
    a plurality of channels with main signal inputs for receiving input signals, wherein input signals each comprise a specific signal component and a signal component common to all input signals, wherein each channel comprises an impedance transforming input amplifier, wherein the apparatus is configured to supply to the first input of each input amplifier a respective input signal and, to the second input, an analog reference signal which is equal for all channels;
    a digital signal processor and one or more analog-digital converters for supplying the signals provided by the input amplifiers to the digital signal processor, wherein the signal processor is configured to convert signals received from the one or more analog-digital converters at least into one or more output signals, wherein the signal processor is configured to process the signals received from the one or more analog-digital converters, for providing a digital reference signal; and
    a digital-analog converter for converting the digital reference signal into said analog reference signal,
    wherein each channel comprises a DC-compensator wherein an input of the DC-compensator is coupled via a digital-analog converter to said signal processor for receiving a control signal therefrom,
    wherein the dc-compensation element is configured to compensate the input signals, received via main inputs, and for providing the compensated input signals to the first inputs of the input amplifiers.

2. The apparatus according to claim 1, wherein the DC-compensator of each channel is controllable by the signal processor such that any DC-offset in the input signal is entirely compensated before the signal is fed into the respective input amplifiers.

3. The apparatus according to claim 1, wherein an output of each input amplifier is operatively connected to an input of the at least one analog-digital converter, directly or indirectly, without presence of a high-pass filter there-between.

4. The apparatus according to claim 1, wherein an output of each input amplifier is operatively connected to an input of the at least one analog-digital converter, directly or indirectly, without presence of a low-pass filter there-between.

5. The apparatus according to claim 1, wherein the signal processor is configured to supply each said control signal under the influence of and/or while utilizing one or more signals obtained from the, or one or more analog-digital converters, respectively.

6. The apparatus according to claim 1, wherein the signal processor is configured to detect a signal offset voltage for each channel, and for adapting said control signal for removing at least a part of a detected signal offset voltage from an input signal to provide a compensated input signal.

7. The apparatus according to claim 1, further comprising a multiplexer and one analog-digital converter.

8. The apparatus according to claim 7, wherein the arrangement is configured such that the multiplexer supplies the signals coming from said channels in a predetermined order to the analog-digital converter.

9. The apparatus according to claim 7, wherein the arrangement is configured such that the multiplexer supplies the signals coming from said channels in a random order to the analog-digital converter.

10. The apparatus according to claim 1, wherein the at least one A/D convertor operates at a resolution lower than 20 bits.

11. The apparatus according to claim 1, wherein the second input of each input amplifier is connected to a respective first impedance wherein the first impedances for all input amplifiers are identical.

12. The apparatus according to claim 1, wherein the second inputs via second impedances, wherein the second impedances are identical for all input amplifiers.

13. The apparatus according to claim 1, wherein the signals comprise physiological measuring signals.

14. The apparatus according to claim 1, wherein the signal processor is configured to digitally average the signals received from the one or more analog-digital converters, for providing a digital reference signal.

15. The apparatus according to claim 1, wherein the DC-compensator comprises a compensation amplifier.

16. A method for processing signals, the method comprising:
    providing a plurality of channels with main signal inputs for receiving input signals, which input signals each comprise a specific signal component and a signal component common to all input signals, wherein each channel comprises an impedance transforming input amplifier, wherein each channel comprises a DC-compensator, wherein an input of DC-compensator is coupled via a digital-analog converter to said signal processor for receiving a control signal therefrom;
    supplying to the first input of each input amplifier a respective input signal and, to the second input, an analog reference signal which is equal for all channels;
    supplying the signals provided by the input amplifiers to the digital signal processor, the supplying being carried out by a digital signal processor and one or more analog-digital converters, wherein the signal processor converts signals received from the one or more analog-digital converters at least into one or more output signals;

wherein the signal processor processes the signals received from the one or more analog-digital converters, for providing a digital reference signal, wherein a digital-analog converter converts the digital reference signal into said analog reference signal;

wherein the DC-compensator compensates the input signals, received via main inputs, and provide the compensated input signals to the first inputs of the input amplifiers.

17. The method according to claim 16, wherein the signal processor provides a first operational state including a full or substantially full dc-compensation for each channel by the DC-compensator.

18. The method according to claim 17, wherein the signal processor provides a second operational state wherein no or only a partial dc-compensation is carried out by the DC-compensator.

19. The method according to claim 16, wherein the input signals include common mode signals and electrode signals, wherein in each channel any DC-offset of the input signal is entirely compensated before the signal is fed into the respective input amplifier.

20. The method according to claim 16, wherein the signals comprise physiological measuring signals.

21. The method according to claim 16, wherein the signal processor is configured to digitally average the signals received from the one or more analog-digital converters, for providing a digital reference signal.

22. The method according to claim 16, wherein the DC-compensator comprises a compensation amplifier.

\* \* \* \* \*